United States Patent
Fu et al.

(10) Patent No.: US 9,969,766 B2
(45) Date of Patent: May 15, 2018

(54) 20(R)-GINSENOSIDE RG3 POLYACYLATED DERIVATIVES, PREPARATION AND APPLICATION THEREOF

(71) Applicant: Li Fu, Dalian (CN)

(72) Inventors: Li Fu, Dalian (CN); Hongyu Fan, Dalian (CN)

(73) Assignee: Li Fu, Dalian (CN)

( * ) Notice: Subject to any disclaimer, the term of this patent is extended or adjusted under 35 U.S.C. 154(b) by 0 days. days.

(21) Appl. No.: 15/536,301

(22) PCT Filed: Dec. 23, 2014

(86) PCT No.: PCT/CN2014/094726
§ 371 (c)(1),
(2) Date: Jun. 15, 2017

(87) PCT Pub. No.: WO2016/095249
PCT Pub. Date: Jun. 23, 2016

(65) Prior Publication Data
US 2017/0327529 A1      Nov. 16, 2017

(30) Foreign Application Priority Data
Dec. 17, 2014   (CN) .......................... 2014 1 0785172

(51) Int. Cl.
*C07J 17/00*      (2006.01)

(52) U.S. Cl.
CPC ............. *C07J 17/005* (2013.01); *C07J 17/00* (2013.01)

(58) Field of Classification Search
None
See application file for complete search history.

(56) References Cited

U.S. PATENT DOCUMENTS

2006/0014704 A1 *   1/2006   Landry .................... C07J 9/00
                                                                   514/26

FOREIGN PATENT DOCUMENTS

| CN | 102603847 | * | 7/2012 |
| CN | 102775461 | * | 11/2012 |
| WO | WO2005116042 A1 | | 12/2005 |

OTHER PUBLICATIONS

Lam et al, Bioorganic and Medicinal Chemistry, vol. 12, 2004, pp. 5587-5593.*
Komori et al., Organic Mass Spectrometry, 1974, vol. 9(8), pp. 744-752.*

* cited by examiner

*Primary Examiner* — Traviss C McIntosh, III
(74) *Attorney, Agent, or Firm* — Greer, Burns & Crain, Ltd.

(57) ABSTRACT

The present invention provides 20(R)-ginsenoside Rg3 polyacylated derivatives of the formula (I) and preparation method and anti-tumor application thereof:

(I)

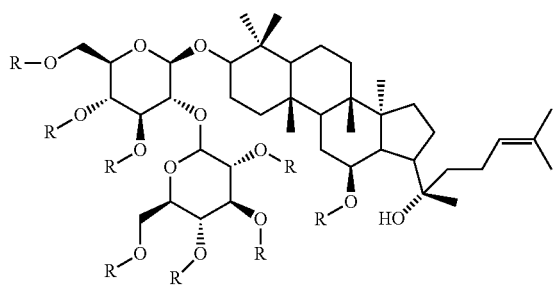

wherein, $R=CH_3(CH_2)nCO$, $n=0\sim5$.

12 Claims, No Drawings

20(R)-GINSENOSIDE RG3 POLYACYLATED DERIVATIVES, PREPARATION AND APPLICATION THEREOF

This application is the U.S. National phase application corresponding to PCT/CN2014/094726 which was assigned an international filing date of Dec. 23, 2014 and associated with publication WO 2016/095249 A1 and which claims priority to Chinese Application 2014107851724 filed on Dec. 17, 2014, the disclosures of which are expressly incorporated herein by reference.

TECHNICAL FIELD

The present invention relates to the field of pharmaceutical chemistry, and in particular, to the present invention relates to a 20 (R)-ginsenoside Rg3 polyacylated derivative and its preparation method thereof, and anti-tumor pharmacological effects of the derivatives.

BACKGROUND ART 20 (R)-Ginsenoside Rg3 is a tetracyclic triterpenoid ginsenoside saponin monomer isolated from Red *ginseng* (Red *ginseng* is a cooked products of *Panax ginseng* C. A. Mey). It is isolated from Korean *ginseng* by the Japanese scholar Kitagawa Hoon in 1980, and its molecular formula is $C_{42}H_{72}O_{13}$, the relative molecular weight of 784.3. 20(R)-Ginsenoside Rg3 has the efficacy of synergistic detoxification, improving the symptoms of qi deficiency, enhancing the immunity of human bodies and so on. In addition, studies have shown that ginsenoside Rg3 still has the role of inhibition of tumor cell proliferation, infiltration and metastasis, can induce apoptosis of liver cancer cells, prostate cancer cells, leukemia cells, cervical cancer cells.

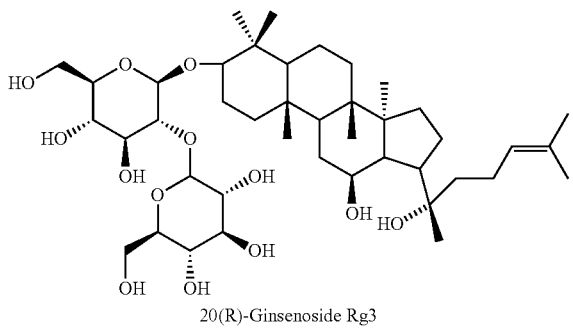

20(R)-Ginsenoside Rg3

Because of its large molecular structure, 20 (R)-ginsenoside Rg3 is not soluble in water and other high polarity solvents, but also not soluble in petroleum ether, chloroform and other low polarity or non-polar solvent; 20 (R)-ginsenoside Rg3 easily soluble in pyridine, ethanol solution (50%~70%), strong acid aqueous solutions (pH<2) and strong alkaline solutions (pH>10). It belongs to the Class IV drugs of Biopharmaceutics Classification System (BCS), and owing to small solubility and transmembrane permeability and low bioavailability, the pharmacological actions of 20(R)-ginsenoside Rg3 are restricted.

In recent years, many scholars have conducted in-depth researches on the polyacylation of natural products, for example, Liu Jikai et al. have synthesized the bergenin pentaacetylate by solid acid catalysis, as shown in the Patent Application which Patent Application number is CN200510010970.0 (Kunming Institute of Botany, Chinese Academy of Sciences). Compared with the raw material bergenin, the animal experiments showed that bergenin pentaacetylate has obvious synergistic pharmacological effect, and can effectively overcome the shortcomings of bergenin, such as poor antitussive and antiasthmatic effect and poor oral absorption.

Mangiferin pentaacetylate, mangiferin heptanoyl, and mangiferin hexaobutyanoyl compounds have been synthesized using catalyst sulfuric acid by Deng Jia Gang research group in Guangxi University of Medical Sciences. (Experiment Traditional Medical Formulae Vol 18, No 24, page 185-189); The pharmacological experiments of mangiferin pentaacetylate, mangiferin propionyl heptaacetylate and mangiferin butyryl hexaacrylate, developed by catalytic synthesis with sulfuric acid (the research group of Deng Jiagang et al., Guangxi Medical University) showed that these three mangiferin derivatives can provide similar pharmacological action as mangiferin, with the dosing of ¼ of mangiferin, indicating that the valence of anti-inflammatory action of the acylated derivatives is better than that of mangiferin (Chinese Journal of Experiment Traditional Medical Formulae Vol 18, No 24, page 185-189), The pharmacological experiments of epigallocatechin gallate octaacetate developed by multi-acylation modification of epigallocatechin gallate (the research group of Tak Hang Chan, Hong Kong Polytechnic University) showed that the derivative has improved stability and enhanced anti-cancer effectiveness (Bioorg & Medicinal Chemistry 12 (2004) 5587-5593). In summary, by esterification modification, the ester derivatives of drugs have improved liposolubility and show increased oil/water distribution coefficient and thus increased transmembrane permeability, leading to improved transmembrane absorption and bioavailability of drugs and ultimately enhanced drug efficacy. However, there is no such research on 20(R)-ginsenoside Rg3, therefore, we design and synthesize 20(R)-ginsenoside Rg3 polyacylated derivatives by alkali catalysis and conduct researches through pharmacological experiments.

SUMMARY OF THE INVENTION

The technical problem to be solved by the present invention is to prepare 20 (R)-ginsenoside Rg3 polyacylated derivatives by chemical synthesis. The invention provides a synthetic 20(R)-ginsenoside Rg3 polyacylated derivative obtained by acylation using 20(R)-ginsenoside Rg3 as starting compound.

The hydroxyl groups of the 20(R)-ginsenoside Rg3 are blocked to improve the lipophilicity and change the oil-water separation coefficient and thus to enhance the intestinal absorption, with the efficacy being improved. Further, the invention also provides a method for preparing 20(R)-ginsenoside Rg3 polyacylated derivatives, which has mild reaction conditions and is suitable for industrial mass production.

Firstly, the invention provides 20(R)-ginsenoside Rg3 polyacylated derivatives (ie 20(R)-ginsenoside Rg3 multi-acylated derivatives) of the formula (I),

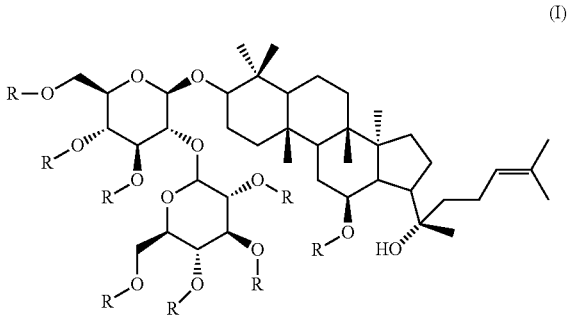

(I)

wherein, $R=CH_3(CH_2)nCO$, n=0~5,
wherein, $R=CH_3(CH_2)nCO$, n=2~4,

Also, the invention provides a pharmaceutical composition comprising a 20(R)-ginsenoside Rg3 polyacylated derivative of the invention and pharmaceutically acceptable excipient.

The pharmaceutically acceptable excipient disclosed herein refer to non-toxic solid, semisolid or liquid fillers, diluents, carriers, pH adjustors, ionic strength modifiers, sustained-release and controlled-release agents, wrapping agents and other pharmaceutical excipients. The excipients used may be adapted to the appropriate form of administration and may be formulated as an adjuvant known to those skilled in the art for injection, lyophilized powder for injection, spray, oral solution, oral suspension, tablet, capsule, Enteric-coated tablets, pills, powders, granules, sustained release or delayed release.

The 20(R)-ginsenoside Rg3 polyacylated derivatives of the first aspect of the invention may be administered by injection or by digestive tract, therefore, the pharmaceutical composition of the invention is preferably an injection formulation or a formulation administered through the digestive tract, in other words, excipients suitable for administration through injection and the digestive tract are particularly preferred.

Wherein, the term "administering to the digestive tract" used herein refers to the form of administration through the digestive tract of patients, including oral administration, gavage administration and enema administration, preferably oral administration, for example, using the auxiliary materials known by a skilled person in the art, oral solutions, oral suspensions, tablets, capsules, enteric coated tablets, pills, powders, granules and sustained-release or delayed-release formulations are provided, wherein, the formulations for administration through injection comprise injections and powder injections.

Also, another aspect of the invention provides a preparation process of 20(R)-ginsenoside Rg3 polyacylated derivatives, comprising the following steps of:

1) dissolving 20(R)-ginsenoside Rg3 in an organic solvent to make a solution of 20(R)-ginsenoside Rg3,
2) adding an acylation agent for esterification,
3) adding water to quench the reaction and adjusting the pH of the mixed solution to 7 with an alkali, and
4) then filtering and re-crystallizing to obtain the final product.

Wherein, the organic solvent of step 1) is selected from triethylamine or anhydrous pyridine, preferably anhydrous pyridine, and the acylation agent of step 2) is acyl chloride or acid anhydride.

Specifically, the acyl chloride is selected from acetyl chloride, propionyl chloride, butyryl chloride, valeryl chloride or hexanoyl chloride; and the acid anhydride is selected from acetic anhydride, propionic anhydride, butyric anhydride, valeric anhydride or caproic anhydride.

Wherein, the reaction temperature of esterification of step 2) is 80-100° C.

Specifically, the time of esterification is 2-5 h.

Specifically, the acylation agent is added to the 20(R)-ginsenoside Rg3 solution at room temperature.

Particularly, the room temperature is 15-35° C.

Wherein, the alkali of step 3) is selected from inorganic alkalis.

Specifically, the inorganic alkali is selected from sodium carbonate, potassium carbonate, sodium bicarbonate or potassium hydrogen carbonate, preferably sodium bicarbonate.

Specifically, the water added in step 3) is ice water, i.e., water of 0° C. temperature, for quenching the esterification process.

Wherein the recrystallization of the 20 (R)-ginsenoside Rg3 polyacylated derivative is carried out using a water/methanol system in step 4).

Still another aspect of the invention provides an application of 20(R)-ginsenoside Rg3 polyacylated derivatives for the preparation of anti-tumor and anti-cancer drugs.

The present invention further provides an application of 20 (R)-gainide saponin Rg3 polyacylated derivatives in the manufacture of medicaments for the control of various animal solid tumors, anti-human lung cancer, anti-breast cancer, anti-gastric cancer, anti-colon cancer and anti-hepatocarcinoma drugs.

The invention has the advantages that: the preparation method of 20(R)-ginsenoside Rg3 polyacylated derivatives of the invention is easily controlled, increases the overall yield of products, and is suitable for industrial mass production.

DETAILED DESCRIPTION OF THE INVENTION

The present invention will be further described by the following embodiments, and the embodiments are to be considered in all respects illustrative rather than limiting of the disclosure described herein. Furthermore, the reagents and materials used in the embodiments are all commercially available, and if insufficient, please refer to Guidebook to Organic Synthesis, guidelines issued by drug regulators and manufacturer's instructions on relevant instruments and reagents.

Example 1

1) 20(R)-Ginsenoside Rg3 (4 g, 5.09 mmol) was added to 180 ml dry anhydrous pyridine and stirred for dissolving, to make a solution of 20(R)-ginsenoside Rg3.

2) At room temperature (15-35° C.), acetyl chloride (0.71 ml, about 10 mmol) was added to the 20 (R)-ginsenoside Rg3 solution.

3) The resulting mixture was heated under stirring and maintained at 80° C. for esterification.

4) After the reaction was maintained at a temperature of 80° C. for 5 hours, the reaction solution was poured into ice water, and a saturated sodium bicarbonate aqueous solution was added to adjust pH to 7, resulting in the precipitation of a large amount of white solid.

5) Filtration gave a white solid, washed with a large amount of water, and recrystallized from water/methanol to give a white powder.

20 (R)-ginsenoside Rg3 octaacetate (3 g) as a white solid, soluble in water, ethanol. After the TLC plate was developed (the chromatographic solution was chloroform/methanol 50:1, Rf was 0.4) and sprayed with 10% $H_2SO_4$-ethanol reagent, then appeared purple. In ESI-MS spectrum, m/z [M+Na] is 1143.6, and molecular weight is 1121.

$^1$H-NMR and $^{13}$C-NMR of 20(R)-ginsenoside Rg3 octoacetate are as follows:

$^1$H-NMR (400 MHz, DMSO-d6) δ (ppm): 5.301-5.255 (t, 1H, J=9.2 Hz), 5.192-5.146 (t, 1H, J=9.2 Hz), 5.062 (s, 1H), 4.891-4.721 (m, 4H), 4.629 (s, 2H), 4.182-4.067 (m, 3H), 3.973-3.911 (m, 3H), 3.630-3.592 (t, 1H, J=1.2 Hz), 3.512 (s, 1H), 3.054-3.053 (d, 1H, J=7.6 Hz), 2.088 (s, 2H), 1.984-1.902 (m, 22H), 1.738 (s, 3H), 1.626-1.210 (m, 18H), 0.992-0.889 (m, 12H), 0.794 (s, 3H), 0.721 (s, 5H);

$^{13}$C-NMR (100 MHz, Pyridin-d5) δ (ppm): 171.88, 171.81, 171.72, 171.61, 171.51, 171.31, 171.19, 171.15 (C=O), 132.05 (C-25), 127.30 (C-24), 104.92 (C-1''), 102.35 (C-1'), 91.57 (C-3), 79.27 (C-2'), 76.78 (C-5''), 74.96 (C-5'), 74.71 (C-2''), 74.71 (C-20), 73.56 (C-3''), 73.25 (C-3'), 72.98 (C-12), 70.79 (C-4''), 70.39 (C-4'), 63.95 (C-6''&6'), 57.54 (C-5), 53.76 (C-14), 51.56 (C-17), 51.47 (C-9), 47.40 (C-13), 44.35 (C-22), 41.17 (C-4), 40.85 (C-8), 40.04 (C-1), 38.18 (C-10), 36.06 (C-7), 32.75 (C-11), 30.09 (C-15), 27.22 (C-28), 25.64 (C-16), 24.96 (C-2), 24.83 (C-26), 22.39 (C-21), 21.93 (C-23), 21.71-21.79 (CH$_3$CO) 18.29 (C-6), 17.65 (C-30), 17.26 (C-27), 16.17 (C-29), 16.13 (C-19), 16.90 (C-18)

Based on the test data of ESI-MS, $^1$H-NMR and $^{13}$C-NMR, it can be determined that the structural formula of 20(R)-ginsenoside Rg3 octoacetate is as follows:

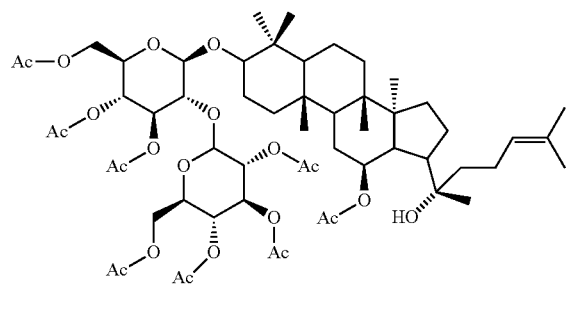

Example 2

1) 20(R)-Ginsenoside Rg3 (4 g, 5.09 mmol) was added to 180 ml dry anhydrous pyridine and stirred for dissolving, to make a solution of 20(R)-ginsenoside Rg3.

2) At room temperature (20-25° C.), N-butyric anhydride (3.07 ml, about 10 mmol) was added to the 20(R)-ginsenoside Rg3 solution condition.

3) The resulting mixture was heated under stirring and maintained at 100° C. for esterification.

4) After the reaction was maintained at a temperature of 100° C. for 5 h, the reactant solution was poured into ice water, and a saturated sodium bicarbonate aqueous solution was added to adjust pH to 7, resulting in the precipitation of a large amount of white solid.

5) Filtration gave a white solid, washed with a large amount of water, and recrystallized from water/methanol to give a white powder.

20(R)-Ginsenoside Rg3 octo-n-butyrate (3 g) is a while solid soluble in water and ethanol. After the TLC plate was developed (the chromatographic solution was petroleum ether/ethyl acetate 3:1, Rf was 0.5) and sprayed with 10% H$_2$SO$_4$-ethanol reagent, then appeared purple. In ESI-MS spectrum, m/z [M+Na] is 1368.27, and molecular weight is 1345.

$^1$H-NMR and $^{13}$C-NMR of 20(R)-Ginsenoside Rg3 octo-n-butyrate are as follows:

$^1$H-NMR (400 MHz, DMSO-d6) δ (ppm): 5.301-5.255 (t, 1H, J=9.2 Hz), 5.192-5.146 (t, 1H, J=9.2 Hz), 5.062 (s, 1H), 4.891-4.721 (m, 4H), 4.629 (s, 2H), 4.182-4.067 (m, 3H), 3.973-3.911 (m, 3H), 3.630-3.592 (t, 1H, J=1.2 Hz), 3.512 (s, 1H), 3.054-3.053 (d, 1H, J=7.6 Hz), 2.35 (m, 12H), 2.32 (s, 2H), 1.984-1.902 (m, 22H), 1.801-1.793 (m, 16H), 1.738 (s, 3H), 0.992-0.889 (m, 16H), 0.794 (s, 3H), 0.721 (s, 5H).

$^{13}$C-NMR (100 MHz, Pyridin-d5) δ (ppm): 172.96, 172.89, 172.62, 172.51, 172.47, 172.28, 172.26, 172.06 (C=O), 130.55 (C-25), 125.81 (C-24), 103.44 (C-1''), 100.82 (C-1'), 90.01 (C-3), 77.41 (C-2'), 77.11 (C-5''), 76.68 (C-5'), 75.47 (C-2''), 72.04 (C-20), 74.43 (C-3''), 73.91 (C-3'), 71.64 (C-12), 69.14 (C-4''), 68.74 (C-4'), 63.30 (C-6'), 63.35 (C-6''), 56.34 (C-5), 51.39 (C-14), 50.16 (C-17), 49.99 (C-9), 48.73 (C-13), 42.59 (C-22), 40.25 (C-4), 40.04 (C-8), 39.25 (C-1), 36.85 (C-10), 35.59-35.90 (CH$_3$CH$_2$CH$_2$CO), 35.01 (C-7), 31.59 (C-11), 31.16 (C-15), 27.22 (C-28), 25.64 (C-16), 24.96 (C-2), 24.83 (C-26), 22.39 (C-21), 21.93 (C-23), 18.42 (C-6), 18.17-18.34 (CH3CH$_2$CH$_2$CO), 17.65 (C-30), 17.26 (C-27), 16.12 (C-29), 16.02 (C-19), 15.40 (C-18), 13.64 (CH$_3$CH$_2$CH$_2$CO).

Based on the test data of ESI-MS, $^1$H-NMR and $^{13}$C-NMR, it can be determined that the structural formula of 20(R)-ginsenoside Rg3 octo-n-butyrate is as follows:

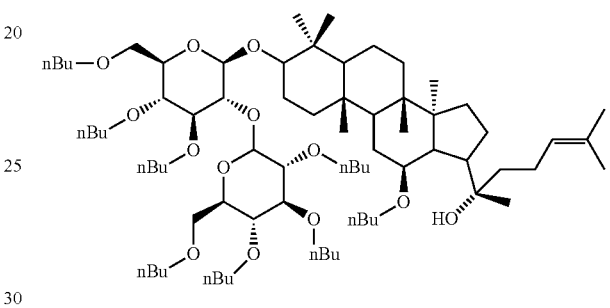

Example 3

1) 20(R)-Ginsenoside Rg3 (4 g, 5.09 mmol) was added to 180 ml dry anhydrous pyridine and stirred for dissolving, to make a solution of 20(R)-ginsenoside Rg3.

2) At room temperature (15-25° C.), N-propionic anhydride (3.07 ml, about 10 mmol) was added to the 20(R)-ginsenoside Rg3 solution.

3) The resulting mixture was heated under stirring and maintained at 80° C. for esterification.

4) After the reaction was maintained at a temperature of 80° C. for 5 h, the reactant solution was poured into ice water, and a saturated sodium bicarbonate aqueous solution was added to adjust pH to 7, resulting in the precipitation of a large amount of white solid.

5) Filtration gave a white solid, washed with a large amount of water, and recrystallized from water/methanol to give a white powder.

20(R)-Ginsenoside Rg3 octo-n-propionate (3 g) is a while solid soluble in water and ethanol.

After the TLC plate was developed (the chromatographic solution was petroleum ether/ethyl acetate 3:1, Rf was 0.4) and sprayed with 10% H$_2$SO$_4$-ethanol reagent, then appeared purple. In ESI-MS spectrum, m/z [M+Na] is 1255.71, and molecular weight is 1233.

$^1$H-NMR and $^{13}$C-NMR of 20(R)-ginsenoside Rg3 octo-propionate are as follows:

$^1$H-NMR (400 MHz, DMSO-d6) δ (ppm): 5.301-5.255 (t, 1H, J=9.2 Hz), 5.192-5.146 (t, 1H, J=9.2 Hz), 5.062 (s, 1H), 4.891-4.721 (m, 4H), 4.629 (s, 2H), 4.182-4.067 (m, 3H), 3.973-3.911 (m, 3H), 3.630-3.592 (t, 1H, J=1.2 Hz), 3.512 (s, 1H), 3.054-3.053 (d, 1H, J=7.6 Hz), 2.29-2.27 (m, 16H), 2.088 (s, 2H), 1.14-1.12 (m, 24H), 1.738 (s, 3H), 0.992-0.889 (m, 16H), 0.794 (s, 3H), 0.721 (s, 5H);

$^{13}$C-NMR (100 MHz, Pyridin-d5) δ (ppm): 175.27, 175.20, 175.04, 174.97, 174.87, 174.70, 174.68, 174.52 (C=O), 132.06 (C-25), 127.31 (C-24), 104.96 (C-1"), 102.38 (C-1'), 91.53 (C-3), 79.14 (C-2'), 77.11 (C-5"), 76.68 (C-5'), 75.47 (C-2"), 72.46 (C-20), 74.43 (C-3"), 73.91 (C-3'), 70.18 (C-12), 70.86 (C-4"), 70.36 (C-4'), 63.81 (C-6"&6'), 57.57 (C-5), 53.86 (C-14), 51.53 (C-17), 51.49 (C-9), 7.40 (C-13), 44.29 (C-22), 41.20 (C-4), 40.87 (C-8), 40.07 (C-1), 38.20 (C-10), 36.09 (C-7), 32.87 (C-11), 30.13 (C-15), 29.54-29.98 (CH3CH2CO), 29.10 (CH3CH2CO), 28.82-28.98 (CH3CH2CO), 27.08 (C-28), 24.24 (C-16), 24.96 (C-2), 24.83 (C-26), 22.39 (C-21), 21.93 (C-23), 19.65 (C-6), 18.97 (C-30), 18.96 (C-27), 17.53 (C-29), 17.50 (C-19), 16.90 (C-18), 10.45-10.58 (CH3CH2CO).

Based on the test data of ESI-MS, $^1$H-NMR and $^{13}$C-NMR, it can be determined that the structural formula of 20(R)-ginsenoside Rg3 octo-n-propionate is as follows:

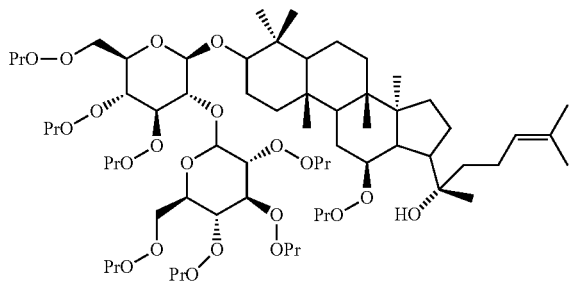

Example 4

1) 20(R)-Ginsenoside Rg3 (4 g, 5.09 mmol) was added to 180 ml dry anhydrous pyridine and stirred for dissolving, to make a solution of 20(R)-ginsenoside Rg3.

2) At room temperature, hexanoyl chloride (1.387 ml, about 10 mmol) was added to the 20(R)-ginsenoside Rg3 solution.

3) The resulting mixture was heated under stirring and maintained at 80° C. for esterification.

4) After the reaction was maintained at a temperature of 80° C. for 5 hours, the reactant solution was poured into ice water, and a saturated sodium bicarbonate aqueous solution was added to adjust pH to 7, resulting in the precipitation of a large amount of white solid.

5) Filtration gave a white solid, washed with a large amount of water, and recrystallized from water/methanol to give a white powder.

20(R)-Ginsenoside Rg3 octo-n-hexanoate (3 g) is a while solid soluble in water and ethanol. After the TLC plate was developed (the chromatographic solution was chloroform/methanol 5:1, Rf was 0.4) and sprayed with 10% $H_2SO_4$-ethanol reagent, then appeared purple. In ESI-MS spectrum, m/z [M+Na] is 1602.2, and molecular weight is 1570.

$^1$H-NMR and $^{13}$C-NMR of 20(R)-ginsenoside Rg3 octo-hexanoate are as follows:

$^1$H-NMR (400 MHz, DMSO-d6) δ (ppm): 5.301-5.255 (t, 1H, J=9.2 Hz), 5.192-5.146, (t, 1H, J=9.2 Hz), 5.062 (s, 1H), 4.891-4.721 (m, 4H), 4.629 (s, 2H), 4.182-4.067 (m, 3H), 3.973-3.911 (m, 3H), 3.630-3.592 (t, 1H, J=1.2 Hz), 3.512 (s, 1H), 3.054-3.053 (d, 1H, J=7.6 Hz), 2.29-2.27 (m, 16H), 2.088 (s, 2H), 1.14-1.12 (m, 24H), 1.738 (s, 3H), 0.992-0.889 (m, 16H), 0.794 (s, 3H), 0.721 (s, 5H)

$^{13}$C-NMR (100 MHz, Pyridin-d5) δ (ppm): 173.27, 173.20, 173.04, 172.98, 172.82, 172.70, 172.67, 172.52 (C=O), 132.06 (C-25), 127.31 (C-24), 104.96 (C-1"), 102.38 (C-1'), 91.53 (C-3), 79.14 (C-2'), 77.11 (C-5"), 76.68 (C-5'), 75.47 (C-2"), 72.46 (C-20), 74.43 (C-3"), 73.91 (C-3'), 70.18 (C-12), 70.86 (C-4"), 70.36 (C-4'), 63.81 (C-6"&6'), 57.57 (C-5), 53.86 (C-14), 51.53 (C-17), 51.49 (C-9), 7.40 (C-13), 44.29 (C-22), 41.20 (C-4), 40.87 (C-8), 40.07 (C-1), 38.20 (C-10), 36.09 (C-7), 33.14-34.28 (CH3CH2CH2CH2CH2CO), 32.87 (C-11), 28.82-28.98 (CH3CH2CH2CH2 CH2CO), 30.13 (C-15), 27.08 (C-28), 24.24 (C-16), 24.96 (C-2), 24.83 (C-26), 22.39 (C-21), 22.48-22.10 (CH3CH2CH2CH2CH2CO), 21.93 (C-23), 19.65 (C-6), 18.97 (C-30), 18.96 (C-27), 17.53 (C-29), 17.50 (C-19), 16.90 (C-18), 14.41-14.67 (CH3CH2CH2CH2CH2CO).

Based on the test data of ESI-MS, $^1$H-NMR and $^{13}$C-NMR, it can be determined that the structural formula of 20(R)-Ginsenoside Rg3 octo-n-hexanoate is as follows:

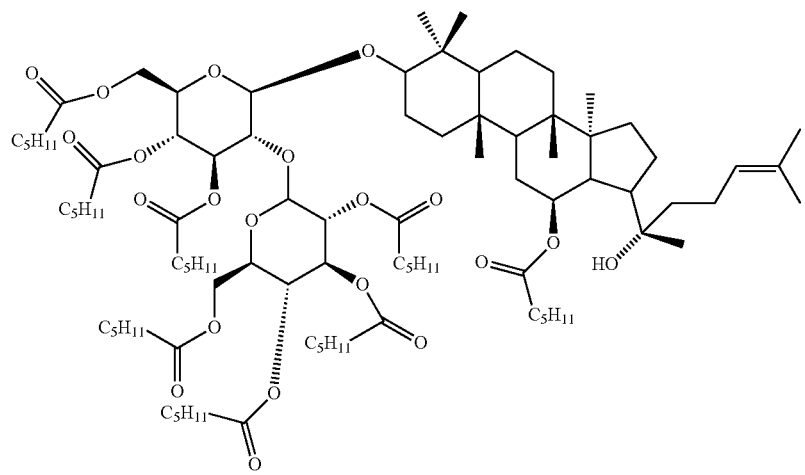

Experiment Example Effect of 20(R)-Ginsenoside Rg3 Polyacylated Derivatives on Inhibiting Tumor Growth 1. Tested Drug 20(R)-ginsenoside Rg3 polyacylated Derivatives:

20(R)-ginsenoside Rg3 octo-acetate, 20(R)-ginsenoside Rg3 octo-n-butyrate and 20(R)-ginsenoside Rg3 octo-n-propionate, provided by Dalian Fusheng natural drug development Co. Ltd., were detected by area normalization method using HPLC UV-detector and evaporative light scattering detector, indicating that the purity were 99.6%, 99.2% and 99.1% respectively.

Preparation Method

Accurately measure a quantity of 20 (R)-ginsenoside Rg3 polyacylated derivatives, add 5% CMC-Na to make the desired concentration of the suspension. Administration volume is 0.5 ml/mouse.

2. Experiment Materials

Positive Drugs:

cyclophosphamide (CTX) for injection, provided by Shanghai Hualian Pharmaceuticals Group, administered once daily, for seven consecutive days;

5 Fu injection solution, provided by Shanghai Xudonghaipu Pharmaceuticals Co., ltd.;

mitomycin (MMC) for injection, provided by Kyowa Hakko Kogyo Co. Ltd.

Tumor Sources:

human breast cancer Bcap-37 model, human lung cancer A549 model, human intestinal cancer LOVO model, human stomach cancer MGC model and human liver cancer QGY model, with tumor cell lines being of the second generation or more, mouse B16 melanoma cell line, mouse Lewis lung cancer model, mouse sarcoma s180 model, all passaged and preserved in Pharmacological Division of Shanghai Institute of Pharmaceutical Industry.

3. Experiment Animals

Origins:

nude mice, 6-week old, 18-22 g/mouse, provided by Laboratory Animal Center of Chinese Academy of Sciences, Shanghai Branch, with certification No. 2001A032.

C57BL/6 mice and Kunming mice, 18-22 g/mouse, provided by Laboratory Animal Center of Chinese Academy of Sciences, Shanghai Branch, with certification SYXK (Shanghai) 2004-0015.

Gender: male or female, the same gender for each batch in experiment

Animal numbers: 10 mice and 10 nude mice for each of positive control group and test group in experiment, and 20 for negative control group.

4. Experiment Design

Dose Settings:

doses for 20(R)-ginsenoside Rg3 octo-acetate, 20(R)-ginsenoside Rg3 octo-n-butyrate and 20(R)-ginsenoside Rg3 octo-n-propionate were set as high-dose group (0.3 mg/kg/d), medium-dose group (0.06 mg/kg/d), and low-dose group (0.012 mg/kg/d).

Dosage regimen: oral administration, twice daily.

human tumor model and cell-inoculated mouse model: po×14 bid;

mouse tumor-inoculated model: po×10 bid.

Control Trial:

negative control group: given with the same volume of 5% CMC-Na as the test group, and the same dosage regimen as the test group.

positive control group: Cyclophosphamide CTX 30 mg/kg, MMC 2 mg/kg and 5Fu 30 mg/kg by intraperitoneal or intravenous administration, once daily, for seven consecutive days.

5. Experiment Method and Key Steps 5.1 Anti-Tumor Test 5.1.1 Subcutaneous Inoculation Model Tumor cells of vigorous growth stage were taken under sterile condition and made into cell suspensions of about $1-2 \times 10^7$/ml by homogenization, the suspensions were inoculated subcutaneously at 0.2 ml/mouse in host mice and repeated on the next day according to the experiment design, the animals in each group were slaughtered after about three weeks, the tumors were collected and weighed, and the tumor inhibition rates were calculated according to the following equation:

tumor inhibition rate %=[(average tumor weight of control group-average tumor weight of treatment group)/average tumor weight of control group]×100%

The same operation was repeated in human tumor xenograft model, except that the feed, packing, cage and contact instruments were all sterilized under high pressure before use and the nude mice were fed in a laminar flow rack. The tumors and tumor-bearing animal weight gains were dynamically measured (tumor size measured using caliper: long diameter/a, short diameter/b, and tumor bulk=$a \times b^2/2$).

5.1.2 Stomach In-Situ Inoculation Model

Two passages in vivo of MGC stomach cancer of vigorous growth stage were taken under sterile condition and made into cell suspensions of about $2 \times 10^7$/ml by homogenization, the cell suspensions (0.05 ml) were surgically injected in greater curvature of stomach in nude mice and repeated on the next day according to the experiment design, and the tumor-bearing host life-extension rates were calculated according to the following equation:

life-extension rate %=average survival days of treatment group/average survival days of control group×100%

5.2 Anti-Tumor Metastasis Test 5.2.1 Tail Vein Inoculation Model

B16 mouse melanoma cells of logarithmic growth stage were taken under sterile condition and made into cell suspensions of about $2.5 \times 10^5$/ml, the cell suspensions were injected 0.2 ml/mouse by tail vein in C57BL/6 mice and repeated on the next day according to the experiment design, the mice were slaughtered after three weeks, the lungs of mice in each group were collected, the colony of metastatic cancer cells in lung per mouse and average colony of tumor cells in each group were calculated, and the tumor inhibition rates were calculated according to the following equation:

tumor inhibition rate %=[(average colony of control group-average colony of treatment group)/average colony of control group]×100%

5.2.2 Spleen Inoculation-Liver Metastasis Model

LOVO intestinal cancer cells (cultured in vitro) of logarithmic growth stage were taken under sterile condition and prepared into cell suspensions of about $1.8 \times 10^7$/ml using RPMI1640 culture medium as diluent. The nude mice were subjected to general anesthesia and cut in belly after routine disinfection to belly skin, the spleens were taken out and inoculated with LOVO intestinal cancer cell suspensions (0.05 ml/mouse) and then restored, the incisions were sutured, and the mice were placed in the cages and then put in the laminar flow rack. The mice were treated on the next day according to the experiment design, observed and recorded for mortality rate of mice in each group, and the life-extension rates were calculated and compared to the negative control group.

5.2.3 Liver In-Situ Inoculation Model

Under sterile condition, the in vivo passage of the second generation of QGY tumor source of vigorous growth stage was prepared into cell suspensions of about $1\text{-}2\times10^7$/ml by homogenization (1:6), and the homogenates were filtered using 100-mesh stainless steel screen, getting ready for use. The nude mice were disinfected routinely and anaesthetized and cut at the xiphoid in the middle of the abdominal cavity to expose the liver, the cell suspensions (0.05 ml) were injected into liver parenchyma using imported 28 ga ½ ml syringes, the abdominal cavity was closed and then sutured layer by layer. The nude mice were fed in the laminar flow rack, with all the feed, packing, cage and contact instruments being sterilized under high pressure before use. The mice were treated on the next day according to the experiment design, observed and recorded for survival time within 45 days in each group, and the survival time was compared to the negative control group, and the life-prolonging rates were calculated.

6. Results 6.1 Results of Anti-Tumor Test of Rg3 Polyacylated Derivatives in Tumor Models The results of anti-tumor test of 20(R)-ginsenoside Rg3 octo-n-propionate, 20(R)-ginsenoside Rg3 octo-n-butyrate and 20(R)-ginsenoside Rg3 octo-acetate in mouse and human tumor models were shown in Table 1 and Table 2.

TABLE 1

Efficacy of 20(R)-ginsenoside Rg3 polyacylated derivatives on mouse Lewis lung cancer (toe subcutaneous inoculation) (n = 3)

| Sample | Dose mg/kg/d | Administration Regimen | Animal numbers (mice) Start/end | Animal body weight (g) Start/end | Tumor-bearing toe weight (g) $\bar{X} \pm SD$ | Tumor inhibition rate % |
|---|---|---|---|---|---|---|
| Rg3-octo-n-propionate high-dose group | 0.3 | po × 14bid | 10/10 | 20.1/24.5 | 0.191 ± 0.105*** | 78.50 |
| Rg3-octo-n-propionate medium-dose group | 0.06 | po × 14bid | 10/10 | 20.6/25.1 | 0.548 ± 0.09*** | 61.58 |
| Rg3-octo-n-propionate low-dose group | 0.012 | po × 14bid | 10/10 | 20.6/24.2 | 0.508 ± 0.07*** | 50.12 |
| Rg3-octo-n-butyrate high-dose group | 0.3 | po × 14bid | 10/10 | 20.6/23.9 | 0.208 ± 0.05*** | 76.66 |
| Rg3-octo-n-butyrate medium-dose group | 0.06 | po × 14bid | 10/10 | 20.9/25.0 | 0.347 ± 0.06*** | 61.00 |
| Rg3-octo-n-butyrate low-dose group | 0.012 | po × 14bid | 10/10 | 20.1/25.2 | 0.440 ± 0.05*** | 50.55 |
| Rg3-octo-acetate high-dose group | 0.3 | po × 14bid | 10/10 | 20.5/23.6 | 0.633 ± 0.08*** | 71.09 |
| Rg3-octo-acetate medium-dose group | 0.06 | po × 14bid | 10/10 | 20.5/24.4 | 0.366 ± 0.09*** | 58.89 |
| Rg3-octo-acetate low-dose group | 0.012 | po × 14bid | 10/10 | 20.1/24.5 | 0.444 ± 0.09*** | 50.15 |
| CTX GROUP | 100 | ip × 14qod | 10/10 | 20.2/21.9 | 0.0541 ± 0.02*** | 93.92 |
| negative control group | 0.5% CMC-Na | po × 14bid | 20/20 | 20.3/28.8 | 0.89 ± 0.11 | |

Compared to the negative control group, ***p value <0.01

TABLE 2

Efficacy of 20(R)-ginsenoside Rg3 polyacylated derivatives on human breast cancer Bcap-37 cells (subcutaneous inoculation) (n = 3)

| Sample | Dose mg/kg/d | Administration Regimen | Animal numbers (mice) Start/end | Animal body weight (g)Start/end | Tumor weight (g) $\bar{X} \pm SD$ | Tumor inhibition rate % |
|---|---|---|---|---|---|---|
| Rg3-octo-n-propionate high-dose group | 0.3 | po × 14bid | 10/10 | 20.9/24.2 | 0.360 ± 0.10*** | 72.09 |
| Rg3-octo-n-propionate medium-dose group | 0.06 | po × 14bid | 10/10 | 20.3/25.1 | 0.502 ± 0.07*** | 61.11 |
| Rg3-octo-n-propionate low-dose group | 0.012 | po × 14bid | 10/10 | 20.7/24.4 | 0.612 ± 0.09*** | 52.58 |
| Rg3-octo-n-butyrate high-dose group | 0.3 | po × 14bid | 10/10 | 20.1/24.2 | 0.380 ± 0.06*** | 70.52 |
| Rg3-octo-n-butyrate medium-dose group | 0.06 | po × 14bid | 10/10 | 20.8/25.1 | 0.610 ± 0.08*** | 60.95 |
| Rg3-octo-n-butyrate low-dose group | 0.012 | po × 14bid | 10/10 | 20.1/24.0 | 0.627 ± 0.07*** | 51.41 |
| Rg3-octo-acetate high-dose group | 0.3 | po × 14bid | 10/10 | 20.3/23.6 | 0.400 ± 0.09*** | 68.98 |
| Rg3-octo-acetate medium-dose group | 0.06 | po × 14bid | 10/10 | 20.2/24.5 | 0.520 ± 0.08*** | 59.69 |
| Rg3-octo-acetate low-dose group | 0.012 | po × 14bid | 10/10 | 20.0/25.7 | 0.672 ± 0.07*** | 47.93 |

TABLE 2-continued

Efficacy of 20(R)-ginsenoside Rg3 polyacylated derivatives on human breast cancer Bcap-37 cells (subcutaneous inoculation) (n = 3)

| Sample | Dose mg/kg/d | Administration Regimen | Animal numbers (mice) Start/end | Animal body weight (g)Start/end | Tumor weight (g) $\bar{X} \pm SD$ | Tumor inhibition rate % |
|---|---|---|---|---|---|---|
| CTX GROUP | 100 | ip × 2qod | 10/10 | 20.4/22.0 | 0.130 ± 0.06*** | 89.90 |
| negative control group | 0.5% CMC-Na | po × 14bid | 20/20 | 20.2/25.5 | 1.29 ± 0.09*** | |

Compared to the negative control group, ***p <0.01

It can be seen from Table 1 and Table 2 that 20(R)-ginsenoside Rg3 octo-n-propionate, 20(R)-ginsenoside Rg3 octo-n-butyrate and 20(R)-ginsenoside Rg3 octo-acetate have inhibitory effect on tumor growth in mouse and human solid tumor models, and the optimal tumor inhibition rate of the treatment group exceed 70%, with a significant difference as compared to the negative control group (p<0.01).

6.2 Results of Anti-Tumor Metastasis Test of Rg3 Polyacylated Derivatives (Namely Rg3 Multi-Acylated Derivatives) in Tumor Metastasis Models The results of anti-tumor metastasis test of 20(R)-ginsenoside Rg3 octo-n-propionate, 20(R)-ginsenoside Rg3 octo-n-butyrate and 20(R)-ginsenoside Rg3 octo-acetate in mouse melanoma B16, S180 and Lewis lung cancer metastasis models and human lung cancer metastasis model were shown in Table 3-6.

TABLE 3

Efficacy of 20(R)-ginsenoside Rg3 polyacylated derivatives on mouse melanoma B16 cells (n = 3)

| Sample | Dose mg/kg/d | Administration Regimen | Animal numbers (mice) Start/end | Animal body weight (g)Start/end | Lung clone numbers (mice) X ± SD | Anti-metastasis rate % |
|---|---|---|---|---|---|---|
| Rg3-octo-n-propionate high-dose group | 0.3 | po × 14bid | 10/10 | 20.1/24.8 | 7.21 ± 7.3*** | 85.01 |
| Rg3-octo-n-propionate medium-dose group | 0.06 | po × 14bid | 10/10 | 19.3/24.3 | 14.82 ± 7.6*** | 69.19 |
| Rg3-octo-n-propionate low-dose group | 0.012 | po × 14bid | 10/10 | 19.6/25.7 | 21.44 ± 7.1*** | 55.42 |
| Rg3-octo-n-butyrate high-dose group | 0.3 | po × 14bid | 10/10 | 20.1/21.1 | 8.07 ± 7.0*** | 83.22 |
| Rg3-octo-n-butyrate medium-dose group | 0.06 | po × 14bid | 10/10 | 19.3/25.3 | 16.29 ± 7.8*** | 66.13 |
| Rg3-octo-n-butyrate low-dose group | 0.012 | po × 14bid | 10/10 | 19.1/25.2 | 23.15 ± 7.9*** | 51.88 |
| Rg3-octo-acetate high-dose group | 0.3 | po × 14bid | 10/10 | 20.0/24.0 | 9.63 ± 7.9*** | 79.98 |
| Rg3-octo-acetate medium-dose group | 0.06 | po × 14bid | 10/10 | 19.4/24.7 | 17.38 ± 7.1*** | 63.87 |
| Rg3-octo-acetate low-dose group | 0.012 | po × 14bid | 10/10 | 19.8/25.2 | 23.62 ± 7.0*** | 50.90 |
| CTX GROUP | 100 | ip × 2qod | 10/10 | 20.1/21.4 | 2.26 ± 2.8*** | 95.30 |
| negative control group | 0.5% CMC-Na | po × 14bid | 20/20 | 19.2/25.5 | 48.10 ± 11.2 | |

Compared to the negative control group, ***p value <0.01

TABLE 4

Efficacy of 20(R)-ginsenoside Rg3 polyacylated derivatives on mouse sarcoma S180 cells (n = 3)

| Sample | Dose mg/kg/d | Administration Regimen | Animal numbers (mice) Start/end | Animal body weight (g) Start/end | Lung clone numbers (mice) X ± SD | Anti-metastasis rate % |
|---|---|---|---|---|---|---|
| Rg3-octo-n-propionate high-dose group | 0.3 | po × 14bid | 10/10 | 20.8/24.1 | 0.47 ± 7.4*** | 84.00 |
| | 0.06 | po × 14bid | 10/10 | 19.8/24.3 | 0.88 ± 7.4*** | 70.12 |
| | 0.012 | po × 14bid | 10/10 | 19.2/25.1 | 1.33 ± 7.2*** | 54.86 |
| Rg3-octo-n-butyrate group | 0.3 | po × 14bid | 10/10 | 20.1/21.2 | 0.55 ± 7.3*** | 81.38 |
| | 0.06 | po × 14bid | 10/10 | 19.1/25.5 | 0.96 ± 7.8*** | 67.51 |
| | 0.012 | po × 14bid | 10/10 | 19.91/25.4 | 1.40 ± 7.7*** | 52.55 |
| Rg3-octo-acetate group | 0.3 | po × 14bid | 10/10 | 20.9/24.1 | 0.62 ± 7.3*** | 78.94 |
| | 0.06 | po × 14bid | 10/10 | 19.2/24.7 | 1.01 ± 7.2*** | 65.80 |
| | 0.012 | po × 14bid | 10/10 | 19.6/25.3 | 1.43 ± 7.1*** | 51.50 |

TABLE 4-continued

Efficacy of 20(R)-ginsenoside Rg3 polyacylated derivatives on mouse sarcoma S180 cells (n = 3)

| Sample | Dose mg/kg/d | Administration Regimen | Animal numbers (mice) Start/end | Animal body weight (g) Start/end | Lung clone numbers (mice) X ± SD | Anti-metastasis rate % |
|---|---|---|---|---|---|---|
| CTX GROUP | 100 | ip × 2qod | 10/10 | 20.2/21.0 | 0.18 ± 2.1*** | 93.84 |
| negative control group | 0.5% CMC-Na | po × 14bid | 20/20 | 19.1/25.0 | 2.95 ± 10.5 | |

Compared to the negative control group, ***p value <0.01

TABLE 5

Efficacy of 20(R)-ginsenoside Rg3 polyacylated derivatives on mouse Lewis lung cancer (subcutaneous inoculation) (n = 3)

| Sample | Dose mg/kg/d | Administration Regimen | Animal numbers (mice) Start/end | Animal body weight (g) Start/end | Lung clone numbers (mice) X ± SD | Anti-metastasis rate % |
|---|---|---|---|---|---|---|
| Rg3-octo-n-propionate high-dose group | 0.3 | po × 14bid | 10/10 | 20.1/24.3 | 0.77 ± 0.11*** | 72.15 |
| | 0.06 | po × 14bid | 10/10 | 19.2/24.4 | 1.09 ± 0.15*** | 60.97 |
| | 0.012 | po × 14bid | 10/10 | 19.6/25.1 | 1.35 ± 0.12*** | 51.55 |
| Rg3-octo-n-butyrate group | 0.3 | po × 14bid | 10/10 | 20.0/21.3 | 0.78 ± 0.11*** | 71.85 |
| | 0.06 | po × 14bid | 10/10 | 19.1/25.4 | 1.08 ± 0.11*** | 61.23 |
| | 0.012 | po × 14bid | 10/10 | 19.5/25.1 | 1.37 ± 0.17*** | 50.87 |
| Rg3-octo-acetate group | 0.3 | po × 14bid | 10/10 | 19.3/24.3 | 0.84 ± 0.15*** | 69.96 |
| | 0.06 | po × 14bid | 10/10 | 19.2/24.7 | 1.14 ± 0.12*** | 58.90 |
| | 0.012 | po × 14bid | 10/10 | 19.1/25.0 | 1.38 ± 0.13*** | 50.30 |
| CTX GROUP | 100 | ip × 2qod | 10/10 | 19.4/21.0 | 0.50 ± 0.09*** | 82.12 |
| negative control group | 0.5% CMC-Na | po × 14bid | 20/20 | 19.3/25.5 | 2.78 ± 0.26 | |

Compared to the negative control group, ***p value <0.01

TABLE 6

Efficacy of 20(R)-ginsenoside Rg3 polyacylated derivatives on human lung cancer A549 cells (subcutaneous inoculation) (n = 3)

| Sample | Dose mg/kg/d | Administration Regimen | Animal numbers (mice) Start/end | Animal body weight (g) Start/end | Lung clone numbers (mice) X ± SD | Anti-metastasis rate % |
|---|---|---|---|---|---|---|
| Rg3 octo-n-propionate high-dose group | 0.3 | po × 14bid | 10/10 | 20.8/24.9 | 0.77 ± 0.13*** | 70.72 |
| | 0.06 | po × 14bid | 10/10 | 19.8/24.0 | 1.09 ± 0.10*** | 61.09 |
| | 0.012 | po × 14bid | 10/10 | 19.2/25.9 | 1.35 ± 0.13*** | 50.58 |
| Rg3-octo-n-butyrate group | 0.3 | po × 14bid | 10/10 | 20.1/21.7 | 0.78 ± 0.13*** | 70.55 |
| | 0.06 | po × 14bid | 10/10 | 19.3/25.3 | 1.08 ± 0.14*** | 60.89 |
| | 0.012 | po × 14bid | 10/10 | 19.91/25.0 | 1.37 ± 0.11*** | 50.01 |
| Rg3-octo-acetate group | 0.3 | po × 14bid | 10/10 | 19.9/24.0 | 0.84 ± 0.13*** | 68.52 |
| | 0.06 | po × 14bid | 10/10 | 19.4/24.5 | 0.81 ± 0.15*** | 57.90 |
| | 0.012 | po × 14bid | 10/10 | 19.7/25.2 | 0.96 ± 0.12*** | 49.91 |
| CTX GROUP | 100 | ip × 2qod | 10/10 | 19.6/21.3 | 0.29 ± 0.12*** | 85.10 |
| negative control group | 0.5% CMC-Na | po × 14bid | 20/20 | 19.2/25.5 | 1.92 ± 0.15 | |

Compared to the negative control group, ***p value <0.01

It can be seen from Table 3-6 that the cancer metastasis inhibition rates of 20(R)-ginsenoside Rg3 octo-n-propionate, 20(R)-ginsenoside Rg3 octo-n-butyrate and 20(R)-ginsenoside Rg3 octo-acetate in mouse melanoma B16, S180 and Lewis lung cancer metastasis models and human lung cancer metastasis model reach up to 70-80%.

6.3 Results of Life-Extension Rate from Anti-Tumor Test of Rg3 Polyacylated Derivatives in Tumor Metastasis Models The results of life-extension rate from anti-tumor test of ginsenoside Rg3 octo-n-propionate, ginsenoside Rg3 octo-n-butyrate and ginsenoside Rg3 octo-acetate in human stomach cancer metastasis, human intestinal cancer metastasis, human liver cancer metastasis models were shown in Table 7-9.

TABLE 7

Efficacy of 20(R)-ginsenoside Rg3 polyacylated derivatives on human stomach cancer MGC cells (in-situ inoculation) (n = 3)

| Sample | Dose mg/kg/d | Administration Regimen | Animal numbers (mice) Start/end | Animal body weight (g) Start/end | Average survival (d) $\bar{X} \pm SD$ | Life extension rate T/C × % |
|---|---|---|---|---|---|---|
| Rg3- | 0.3 | po × 14bid | 10/10 | 20.1/24.5 | 48.30 ± 0.15*** | 212.11 |
| octo-n-propionate | 0.06 | po × 14bid | 10/10 | 19.6/24.3 | 43.15 ± 0.15*** | 189.52 |
| high-dose group | 0.012 | po × 14bid | 10/10 | 19.4/25.8 | 39.23 ± 0.18*** | 172.30 |
| Rg3-octo-n- | 0.3 | po × 14bid | 10/10 | 20.3/21.2 | 47.86 ± 0.15*** | 210.19 |
| butyrate group | 0.06 | po × 14bid | 10/10 | 19.1/25.4 | 42.22 ± 0.12*** | 185.44 |
|  | 0.012 | po × 14bid | 10/10 | 19.1/25.4 | 39.35 ± 0.15*** | 172.83 |
| Rg3-octo-acetate | 0.3 | po × 14bid | 10/10 | 19.7/24.1 | 46.04 ± 0.12*** | 202.19 |
| group | 0.06 | po × 14bid | 10/10 | 19.6/24.6 | 41.21 ± 0.11*** | 180.98 |
|  | 0.012 | po × 14bid | 10/10 | 19.8/25.4 | 38.84 ± 0.14*** | 170.56 |
| CTX GROUP | 100 | ip × 2qod | 10/10 | 19.5/21.1 | 41.22 ± 3.5*** | 181.01 |
| negative control group | 0.5% CMC-Na | po × 14bid | 20/20 | 19.5/25.2 | 22.77 ± 2.14 |  |

Compared to the negative control group, ***p value <0.01

TABLE 8

Efficacy of 20(R)-ginsenoside Rg3 polyacylated derivatives on human intestinal cancer LOVO cells (spleen inoculation)

| Sample | Dose mg/kg/d | Administration Regimen | Animal numbers (mice) Start/end | Animal body weight (g)Start/end | Average survival (d) $\bar{X} \pm SD$ | Life extension rate T/C × % |
|---|---|---|---|---|---|---|
| Rg3- | 0.3 | po × 14bid | 10/10 | 20.1/24.5 | 33.21 ± 5.5*** | 243.11 |
| octo-n-propionate | 0.06 | po × 14bid | 10/10 | 19.6/24.3 | 26.08 ± 4.2*** | 190.89 |
| high-dose group | 0.012 | po × 14bid | 10/10 | 19.4/25.8 | 24.63 ± 3.9*** | 180.33 |
| Rg3-octo-n- | 0.3 | po × 14bid | 10/10 | 20.3/21.2 | 32.77 ± 4.1*** | 239.88 |
| butyrate group | .06 | po × 14bid | 10/10 | 19.1/25.4 | 25.67 ± 3.9*** | 187.94 |
|  | 0.012 | po × 14bid | 10/10 | 19.1/25.4 | 24.60 ± 5.8*** | 180.12 |
| Rg3-octo-acetate | 0.3 | po × 14bid | 10/10 | 19.7/24.1 | 31.50 ± 5.1*** | 230.59 |
| group | 0.06 | po × 14bid | 10/10 | 19.6/24.6 | 25.80 ± 4.8*** | 188.90 |
|  | 0.012 | po × 14bid | 10/10 | 19.8/25.4 | 24.59 ± 4.5*** | 179.99 |
| CTX GROUP | 100 | ip × 2qod | 10/10 | 19.5/21.1 | 29.36 ± 3.3*** | 214.91 |
| negative control group | 0.5% CMC-Na | po × 14bid | 20/20 | 19.5/25.2 | 13.66 ± 2.31 |  |

Compared to the negative control group, ***p value <0.01

TABLE 9

Efficacy of 20(R)-ginsenoside Rg3 polyacylated derivatives on human liver cancer QGY cells (in-situ inoculation)

| Sample | Dose mg/kg/d | Administration Regimen | Animal numbers (mice) Start/end | Animal body weight (g)Start/end | Average survival (d) $\bar{X} \pm SD$ | Life extension rate T/C × % |
|---|---|---|---|---|---|---|
| Rg3-octo-n- | 0.3 | po × 14bid | 10/10 | 20.2/24.2 | 44.19 ± 5.3*** | 189.23 |
| propionate | 0.06 | po × 14bid | 10/10 | 19.5/24.1 | 39.72 ± 4.9*** | 170.10 |
| high-dose group | 0.012 | po × 14bid | 10/10 | 19.8/25.3 | 37.49 ± 3.5*** | 160.55 |
| Rg3-octo-n- | 0.3 | po × 14bid | 10/10 | 20.1/21.8 | 43.40 ± 4.8*** | 185.85 |
| butyrate group | 0.06 | po × 14bid | 10/10 | 19.3/25.6 | 39.51 ± 3.9*** | 169.22 |
|  | 0.012 | po × 14bid | 10/10 | 19.2/25.6 | 37.36 ± 5.3*** | 160.01 |
| Rg3-octo-acetate group | 0.3 | po × 14bid | 10/10 | 19.3/24.8 | 42.49 ± 5.0*** | 181.98 |
|  | 0.06 | po × 14bid | 10/10 | 19.1/24.3 | 38.90 ± 4.1*** | 166.59 |
|  | 0.012 | po × 14bid | 10/10 | 19.1/25.2 | 37.26 ± 4.5*** | 159.58 |
| CTX GROUP | 100 | ip × 2qod | 10/10 | 19.1/21.0 | 37.23 ± 3.4*** | 159.44 |
| negative control group | 0.5% CMC-Na | po × 14bid | 20/20 | 19.6/25.1 | 23.35 ± 2.3 |  |

Compared to the negative control group, ***p value <0.01

It can be seen from Table 7-9 that 20(R)-ginsenoside Rg3 octo-n-propionate, 20(R)-ginsenoside Rg3 octo-n-butyrate and 20(R)-ginsenoside Rg3 octo-acetate can significantly increase the survival time in human stomach cancer, human intestinal cancer and human liver cancer models, with obvious life-prolonging effect. Among the groups, the high-dose groups of 20(R)-ginsenoside Rg3 octo-n-propionate, 20(R)-ginsenoside Rg3 octo-n-butyrate and 20(R)-ginsenoside Rg3 octo-acetate showed obvious life-prolonging effect on human stomach, human intestinal cancer and human liver cancer, all being better than the positive control group; and the low-dose groups showed the similar life-prolonging effect as the positive control group.

The invention claimed is:

1. A 20(R)-ginsenoside Rg3 polyacylated derivative of the formula (I),

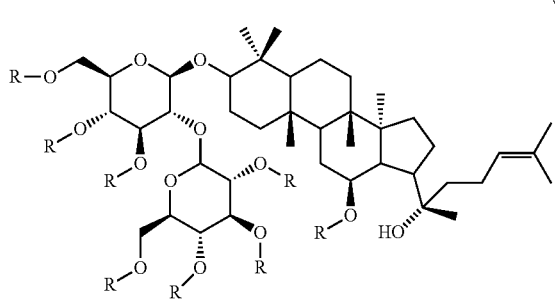

(I)

wherein, R=$CH_3(CH_2)nCO$, n=1~5.

2. A preparation method of the 20(R)-ginsenoside Rg3 polyacylated derivative of the formula (I) of claim 1, characterized by comprising the following steps of:
1) dissolving 20(R)-ginsenoside Rg3 in an organic solvent to make a solution of 20(R)-ginsenoside Rg3,
2) adding an acylation agent for esterification and performing an esterification reaction at a temperature in the range from 80° C. to 100° C.,
3) adding water to quench the reaction and adjusting the pH of the mixed solution to 7 with an alkali, and
4) filtering and re-crystallizing to obtain the final product.

3. The method of claim 2, characterized in that the organic solvent of step 1) is anhydrous pyridine.

4. The method of claim 2, characterized in that the acylation agent of step 2) is selected from the group consisting of acyl chloride or acid anhydride.

5. The method of claim 4, characterized in that the acyl chloride is selected from the group consisting of propionyl chloride, butyryl chloride, valeryl chloride or hexanoyl chloride; and the acid anhydride is selected from the group consisting of propionic anhydride, butyric anhydride, valeric anhydride or caproic anhydride.

6. The method of claim 2, characterized in that the alkali in step 3) is inorganic alkalis.

7. The method of claim 6, characterized in that the inorganic alkali is selected from the group consisting of sodium carbonate, potassium carbonate, sodium bicarbonate or potassium hydrogen carbonate.

8. An anti-cancer drug comprising the 20(R)-ginsenoside Rg3 polyacylated derivative of claim 1.

9. A method of cancer treatment, the method comprising administering to a cancer patient the 20(R)-ginsenoside Rg3 polyacylated derivative of claim 1.

10. The anti-cancer drug of claim 8, wherein the cancer is a solid tumor.

11. The method of claim 9, wherein the cancer patient is treated for a solid tumor.

12. The method of claim 9, wherein the cancer is selected from the group consisting of lung cancer, breast cancer, stomach cancer, intestinal cancer and liver cancer.

* * * * *